(12) United States Patent
Fujii

(10) Patent No.: US 7,682,339 B2
(45) Date of Patent: Mar. 23, 2010

(54) INDWELLING NEEDLE DEVICE

(75) Inventor: Ryoji Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 172 days.

(21) Appl. No.: 11/887,038

(22) PCT Filed: Feb. 14, 2006

(86) PCT No.: PCT/JP2006/302511

§ 371 (c)(1),
(2), (4) Date: Sep. 24, 2007

(87) PCT Pub. No.: WO2006/100847

PCT Pub. Date: Sep. 28, 2006

(65) Prior Publication Data

US 2009/0082733 A1    Mar. 26, 2009

(30) Foreign Application Priority Data

Mar. 24, 2005 (JP) .............................. 2005-086545
Feb. 8, 2006 (JP) .............................. 2006-031500

(51) Int. Cl.
*A61M 5/178* (2006.01)
(52) U.S. Cl. ............................................... 604/164.08
(58) Field of Classification Search ............ 604/164.08, 604/513
See application file for complete search history.

(56) References Cited

U.S. PATENT DOCUMENTS

| | | | | |
|---|---|---|---|---|
| 3,598,118 A | * | 8/1971 | Warren | 604/508 |
| 4,417,887 A | * | 11/1983 | Koshi | 604/162 |
| 4,846,805 A | * | 7/1989 | Sitar | 604/165.04 |
| 5,007,901 A | * | 4/1991 | Shields | 604/110 |
| 5,051,109 A | * | 9/1991 | Simon | 604/263 |
| 5,088,982 A | * | 2/1992 | Ryan | 604/110 |

(Continued)

FOREIGN PATENT DOCUMENTS

JP          10-258123          9/1998

(Continued)

OTHER PUBLICATIONS

International Search Report from corresponding PCT/JP2006/302511, mailed May 16, 2006.

*Primary Examiner*—Nicholas D Lucchesi
*Assistant Examiner*—Diva Ranade
(74) *Attorney, Agent, or Firm*—Hamre, Schumann, Mueller & Larson, P.C.

(57) ABSTRACT

An indwelling needle device includes a shield tube with a flexible outer needle fixed at a front end, a hub movable in a lumen of the shield tube, an infusion tube attached to an end thereof, a rigid inner needle at a front end part of the hub and insertable into a lumen of the outer needle. A lateral penetration path penetrates to a lumen of the hub. A space is provided between an outer surface of the hub and an inner surface of the shield tube. A sealing section is on the outer surface of the hub. The outer peripheral surface of the hub forms engagement recesses. A rear-end-side engagement projection is on the inner surface of the shield tube and engages with the engagement recesses. Hub side walls, with a communication area opening, couple with the front end of the hub. The hub can be small in size.

16 Claims, 7 Drawing Sheets

U.S. PATENT DOCUMENTS

| | | | |
|---|---|---|---|
| 5,120,320 A * | 6/1992 | Fayngold | 604/177 |
| 5,338,306 A * | 8/1994 | Srivatsa | 604/165.02 |
| 5,385,554 A * | 1/1995 | Brimhall | 604/168.01 |
| 5,590,696 A * | 1/1997 | Phillips et al. | 141/47 |
| 5,607,405 A * | 3/1997 | Decker et al. | 604/264 |
| 5,674,201 A * | 10/1997 | Steinman | 604/165.03 |
| 5,676,656 A * | 10/1997 | Brimhall | 604/165.03 |
| 5,893,844 A | 4/1999 | Misawa | |
| 6,485,473 B1 * | 11/2002 | Lynn | 604/256 |
| 6,629,956 B1 * | 10/2003 | Polidoro et al. | 604/164.01 |
| 6,632,198 B2 * | 10/2003 | Caizza | 604/110 |
| 6,730,062 B2 * | 5/2004 | Hoffman et al. | 604/164.02 |
| 6,740,063 B2 * | 5/2004 | Lynn | 604/256 |
| 2003/0220612 A1 * | 11/2003 | Hiejima | 604/165.03 |
| 2004/0044313 A1 * | 3/2004 | Nakajima | 604/167.02 |
| 2004/0225260 A1 * | 11/2004 | Villa et al. | 604/164.01 |
| 2006/0047247 A1 * | 3/2006 | Anders | 604/164.08 |
| 2007/0250011 A1 * | 10/2007 | Lee | 604/165.03 |
| 2008/0065027 A1 * | 3/2008 | Sharp | 604/220 |
| 2008/0097344 A1 * | 4/2008 | McKinnon et al. | 604/263 |
| 2008/0243086 A1 * | 10/2008 | Hager et al. | 604/198 |

FOREIGN PATENT DOCUMENTS

| | | |
|---|---|---|
| JP | 2001-245980 | 9/2001 |
| WO | WO 2004/000407 | 12/2003 |

\* cited by examiner

INDWELLING NEEDLE DEVICE

TECHNICAL FIELD

The present invention relates to an indwelling needle device having a function of preventing an accidental puncture, which includes a flexible outer needle and a rigid inner needle that are configured so that puncturing is carried out with use of the inner needle projected out of the outer needle and thereafter the inner needle can be retracted through the outer needle.

BACKGROUND ART

Indwelling needle devices are used widely for procedures such as infusion, blood transfusion, extracorporeal blood circulation and the like, and various configuration examples of the same are known. For example, a winged indwelling needle has a configuration where a needle is held at a front end of a hub that has wing parts, and an infusion tube is attached to a rear end of the hub. During infusion, the wing parts are fastened onto the patient's arm or the like by adhesion tapes or the like so as to maintain the insertion of the needle.

Meanwhile, contamination and infection due to accidental punctures of injection needles, insertion needles and the like have been a problem in medical centers. As a structure for preventing an accidental puncture, a structure has been known where a cylindrical shield having wing parts is provided slidably with respect to a hub having a needle. That is, by sliding the cylindrical shield, the needle either can be exposed or housed in the shield, and when the injection needle and the insertion needle are discarded after use, each of them can be slid into the shield so as to be housed therein.

Further, when a metal needle is indwelled in a blood vessel, the blood vessel is damaged in some cases. As a structure to cope with this, the following structure of an indwelling needle has been known; the structure includes a flexible outer needle and a rigid inner needle that are configured so that insertion is carried out with use of the inner needle projected out of the outer needle and thereafter the inner needle can be retracted through the outer needle. In this case also, to prevent an accidental puncture, the foregoing structure combined with a cylindrical shield as described above has been known also, which allows the inner needle to be housed in the cylindrical shield in a state where the outer needle is indwelled.

In the indwelling needle of the double-needle structure, which includes the above-described cylindrical shield for preventing an accidental puncture, an infusion tube is connected with a hub that holds the inner needle. In a state in which the inner needle is retracted into the cylindrical shield, a flow path from the infusion tube to a lumen of the outer needle passes a lumen of the inner needle. The lumen of the inner needle, however, has a small diameter, and this makes it difficult to provide a sufficient flow rate.

To provide a sufficient flow rate, it has been attempted to utilize a space formed between an outer peripheral surface of the hub that holds the inner needle and an inner peripheral surface of the cylindrical shield as a flow path to be added to the flow path formed by the lumen of the inner needle. In other words, it has been attempted to adopt a structure in which the space formed between the outer peripheral surface of the hub and the inner peripheral surface of the cylindrical shield communicates with the lumen of the outer needle via a gap between the outer needle and the inner needle, and an opening is formed in the hub so as to allow the foregoing space and the lumen of the hub to communicate with each other. Since it is possible to make the lumen of the hub broader than the lumen of the inner needle, an increased flow rate can be provided as a whole as compared with the flow rate in the case where only the lumen of the inner needle is available as a flow path (see, e.g., Patent Document 1).

Patent document 1: JP 2001-245980 A

DISCLOSURE OF INVENTION

Problem to be Solved by the Invention

However, the above-described indwelling needle device of the conventional example has only one opening formed in the hub, which is not enough to provide a sufficient flow rate. On the other hand, the opening of an excessively large size weakens the structure of the coupling of the front end part of the hub for holding the inner needle, which is positioned on the front end side with respect to the opening, with the rear end part of the hub. Thus, sufficient strength for safe use cannot be provided. Further, if a mechanism for housing the inner needle in the cylindrical shield so as to hold the inner needle is provided separately from the opening, the hub has to have a greater length in the axis direction, whereby the device as a whole becomes bulky.

It is an object of the present invention to provide an indwelling needle device in which an opening for communication with a lumen of the hub is configured so as to have a sufficient cross-sectional area, while side walls of a hub where the foregoing opening is positioned are coupled stably and firmly with a front end part of the hub for holding an inner needle, and the hub can be configured to be small in size.

Means for Solving Problem

An indwelling needle device of the present invention includes: a shield tube in a substantially cylindrical form; a flexible outer needle fixed at a front end part of the shield tube; a hub inserted in a lumen of the shield tube so as to be movable in an axis direction, an infusion tube being attached to a rear end of the hub; and a rigid inner needle that is fixed at a front end part of the hub and that is insertable into a lumen of the outer needle, whereby when the hub is positioned in a front end part of the lumen of the shield tube, the inner needle penetrates the lumen of the outer needle and is projected out, and the inner needle can be housed in the lumen of the shield tube by moving the hub toward a rear end side of the lumen of the shield tube.

To solve the above-described problems, in an indwelling needle device of the first configuration of the present invention, the hub is provided with a lateral penetration path that penetrates from a periphery to a lumen of the hub, so that a space formed between an outer peripheral surface of the hub and an inner peripheral surface of the shield tube communicates with the lumen of the hub via the lateral penetration path. A sealing section is provided on the outer peripheral surface of the hub, at a position on a rear end side with respect to the lateral penetration path in the hub, so as to keep liquid tightness of the space formed between the outer peripheral surface of the hub and the inner peripheral surface of the shield tube. Engagement recesses are formed by outer peripheral surfaces of side wall portions on both sides of the lateral penetration path in the hub. Further, a rear-end-side engagement projection is formed at a rear-end-side position on the inner peripheral surface of the shield tube, so as to be engageable with the engagement recesses in a state in which the inner needle is housed in the lumen of the shield tube.

In an indwelling needle device of the second configuration of the present invention, the hub is provided with a lateral penetration path that penetrates from a periphery to a lumen of the hub, so that a space formed between an outer peripheral surface of the hub and an inner peripheral surface of the shield tube communicates with the lumen of the hub via the lateral penetration path. A sealing section is provided on the outer peripheral surface of the hub, at a position on a rear end side with respect to the lateral penetration path in the hub, so as to keep liquid tightness of the space formed between the outer peripheral surface of the hub and the inner peripheral surface of the shield tube. Front-end-side engagement recesses are formed by outer peripheral surfaces of side wall portions on both sides of the lateral penetration path in the hub. A rear-end-side engagement recess is formed on the outer peripheral surface of the hub, at a position on a rear end side with respect to the sealing section. Further, a front-end-side engagement projection is formed at a front-end-side position on the inner peripheral surface of the shield tube, so as to be engageable with the front-end-side engagement recesses of the hub in a state in which the inner needle is projected out of the outer needle. A rear-end-side engagement projection is formed at a rear-end-side position on the inner peripheral surface of the shield tube, so as to be engageable with the rear-end-side engagement recess in a state in which the inner needle is housed in the lumen of the shield tube.

EFFECTS OF THE INVENTION

With the above-described configuration in which the front-end-side engagement recesses and the lateral penetration path are provided at the same position in the axis direction and the engagement recesses are provided in pair, a structure can be achieved in which a sufficient flow path cross-sectional area is provided by the lateral penetration path, while the side walls where the engagement recesses are formed are coupled with the front end part of the hub for holding the inner needle with sufficient firmness and stability. Moreover, the hub can be configured to be very small in size.

Figure 1:
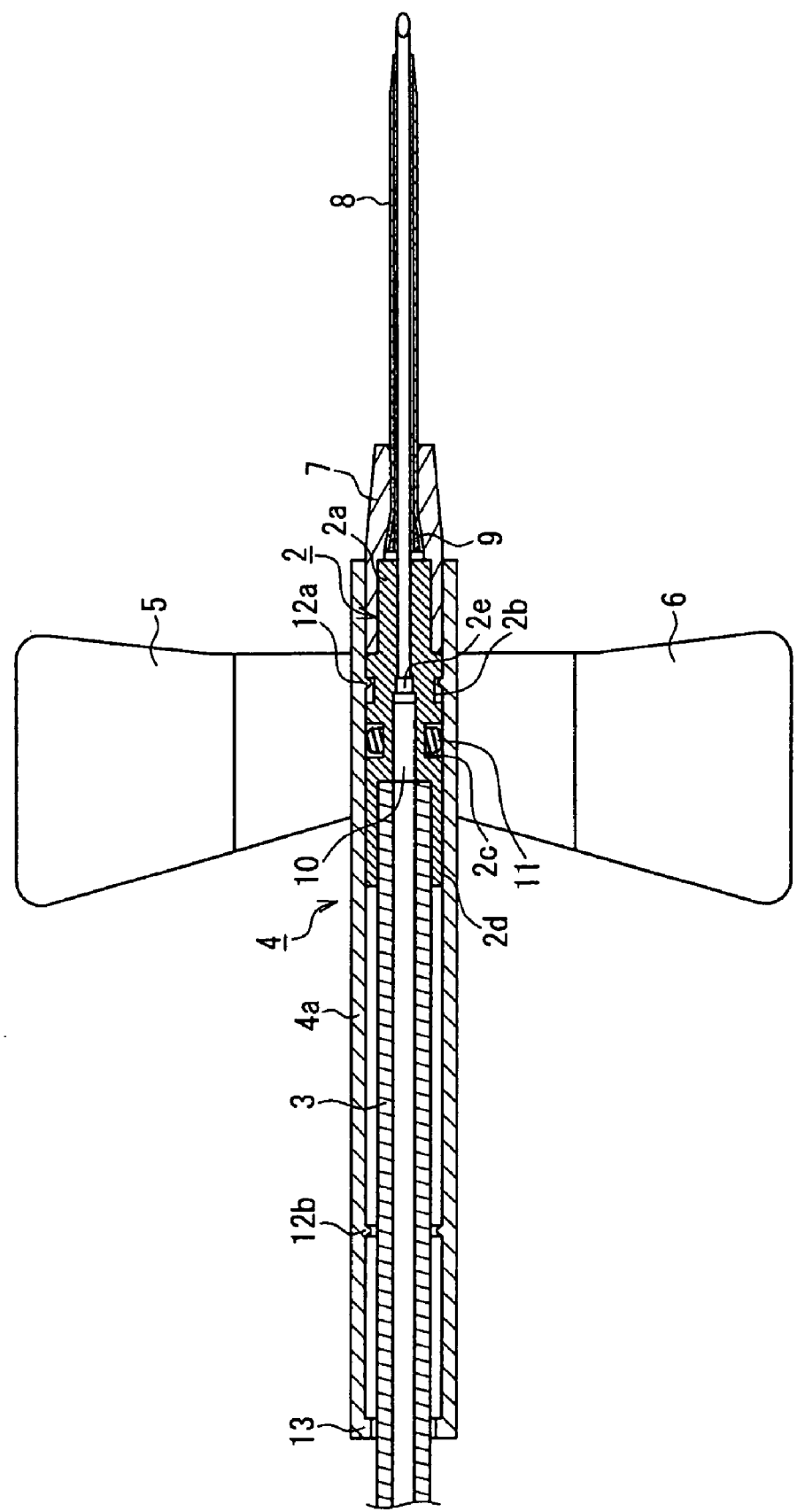
FIG. 1 is a cross-sectional view showing an indwelling needle device according to Embodiment 1 of the present invention.

| Description of Reference Numerals | |
|---|---|
| 1 | inner needle |
| 1a | side hole |
| 2 | hub |
| 2a | front part |
| 2b | engagement recess (front-end-side engagement recess) |
| 2c | sealing circular recess |
| 2d | rear part |
| 2e | lateral penetration path |
| 3 | tube |
| 4 | winged shield |
| 4a | shield tube |
| 5, 6 | wing part |
| 7 | outer hub |
| 8 | outer needle |
| 9 | crimping member |
| 10 | lumen |
| 11 | O-ring |
| 12a | front-end-side engagement projection |
| 12b | rear-end-side engagement projection |
| 13 | stopper |
| 14, 15 | space |
| 16 | axis-direction groove |

BEST MODE FOR CARRYING OUT THE INVENTION

In the indwelling needle device of the first configuration of the present invention, the shield tube further may include a front-end-side engagement projection at a front-end-side position on the inner peripheral surface of the shield tube, the front-end-side engagement projection being engageable with the engagement recesses of the hub in a state in which the inner needle is projected out of the outer needle.

In any one of the indwelling needle devices of the above-described configurations, an outer diameter of the hub at a position on a front end side with respect to the lateral penetration path may be smaller than an outer diameter of the hub at a position on a rear end side.

Further, the indwelling needle device may be configured so that the front-end-side engagement projection and the rear-end-side engagement projection are formed as circular projections extending in a circumferential direction of the inner peripheral surface of the shield tube.

Further, the indwelling needle device may be configured so that the sealing section is composed of a circular groove formed on the outer peripheral surface of the hub and an O-ring placed in the circular groove.

Further, the indwelling needle device may be configured so that a diameter of the lumen of the hub at a position on the rear end side with respect to a position at which the lumen communicates with the lateral penetration path is greater than a diameter of the lumen of the inner needle, and equal to or smaller than an inner diameter of the infusion tube.

Further, the indwelling needle device may be configured so that the hub further includes, on the outer peripheral surface thereof, an axis-direction groove for allowing a space formed between an outer peripheral surface of a front end part of the hub and the inner peripheral surface of the shield tube to communicate with the lateral penetration path.

Further, the indwelling needle device may be configured so that the inner needle has a side hole in its front end part, the side hole being positioned on the rear end side with respect to a position at which a front end part of the outer needle is in contact with the inner needle in a state in which a projected portion of the inner needle out of an end of the outer needle has the maximum length.

The following will describe embodiments of the present invention more specifically while referring to the drawings.

Embodiment 1

Figure 2:
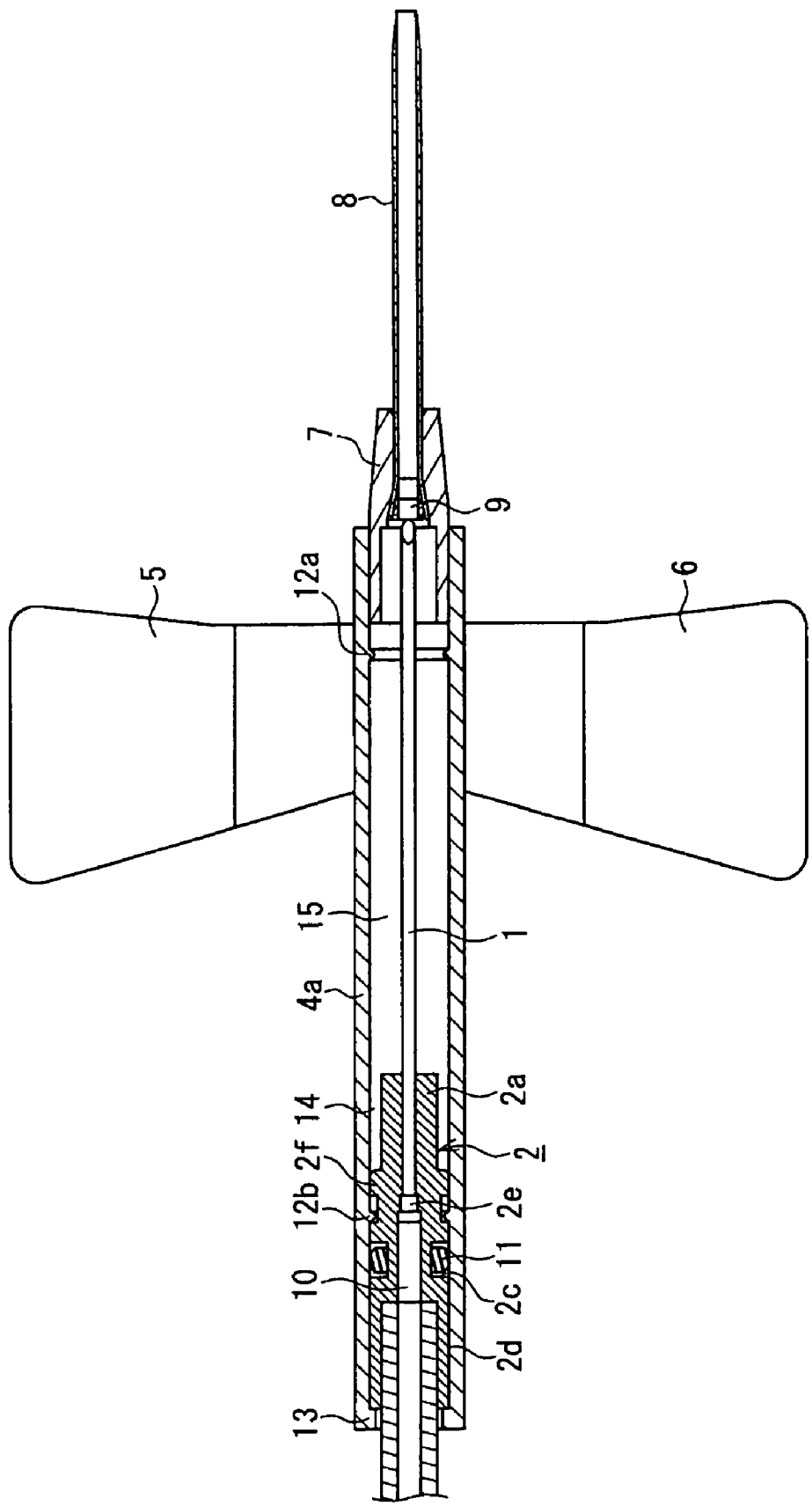
FIG. 2 is a cross-sectional view showing a state of the indwelling needle device when it is indwelled or when it is disposed.

FIG. 1 is a cross-sectional view of an indwelling needle device according to Embodiment 1 of the present invention, taken along an axis direction thereof. FIG. 2 is a cross-sectional view showing a state of the indwelling needle device when an inner needle of the indwelling needle device is retracted in the cylindrical shield.

"1" denotes an inner needle made of a metal, which is fixed at a front end part of an inner hub 2 made of a resin. A tube 3 is attached to a rear part of the inner hub 2. "4" denotes a winged shield, which is composed of a resin-made shield tube 4a in a substantially cylindrical shape, and left and right wing parts 5 and 6. The inner needle 1 and the inner hub 2 are inserted in a lumen of the shield tube 4a so as to be movable in the axis direction. The left and right wing parts 5 and 6 are provided at a front end part of the shield tube 4a, that is, at the end part on the side where the inner needle 1 is projected. The wing parts 5 and 6 are coupled with both lateral sides of an outer peripheral surface of the shield tube 4a, respectively, and have shapes that are symmetric with respect to the axis of the shield tube 4a. As a material for forming the shield tube 4a, a resin material having flexibility such as polyethylene, a vinyl chloride resin, or another elastomer can be used. As a material for forming the inner hub 2, polycarbonate, for example, can be used.

An outer hub 7 is fixed at the front end part of the shield tube 4a, and an outer needle 8 is attached in a lumen of the outer hub 7 and is fixed by a crimping member 9. The inner needle 1 is inserted in a lumen of the outer needle 8 in a manner such that a front end of the inner needle 1 is projected out of the outer needle 8. The outer needle 8 is made of a resin material, for example, a polyurethane-based elastomer.

The inner hub 2 is composed of a front part 2a, a rear part 2d, and an intermediate part between the foregoing two. The rear part 2d and the intermediate part have an outer diameter such that the foregoing parts are fitted exactly in the lumen of the shield tube 4a. The front part 2a has a diameter smaller than the diameter of the other parts, and hence, a space is formed between the front part 2a and an inner peripheral surface of the shield tube 4a, as will be described later. The inner needle 1 is inserted in a lumen of the front part 2a. The tube 3 is inserted in a lumen of the rear part 2d. The diameter of the lumen 10 in the intermediate part is set to be greater than the diameter of the lumen of the inner needle 1, and equal to or smaller than the inner diameter of the tube 3.

Engagement recesses 2b and a sealing circular recess 2c are formed on an outer peripheral surface of the inner hub 2 in the intermediate part. Additionally, a lateral penetration path 2e is formed thereon at the same position with respect to the axis direction as the position of the engagement recesses 2b. The sealing circular recess 2c is positioned on a rear end side with respect to the engagement recesses 2b and the lateral penetration path 2e. An O-ring 11 is attached in the sealing circular recess 2c, thereby forming a sealing section. With this, the liquid tightness of the space between the outer peripheral surface of the inner hub 2 and the inner peripheral surface of the shield tube 4a can be maintained. On the inner peripheral surface of the shield tube 4a, a front-end-side engagement projection 12a in a circular shape and a rear-end-side engagement projection 12b in a circular shape are provided at positions corresponding to the engagement recesses 2b. On an inner peripheral surface of the rear end part of the shield tube 4a, a stopper 13 in a circular shape is formed.

Figure 3:
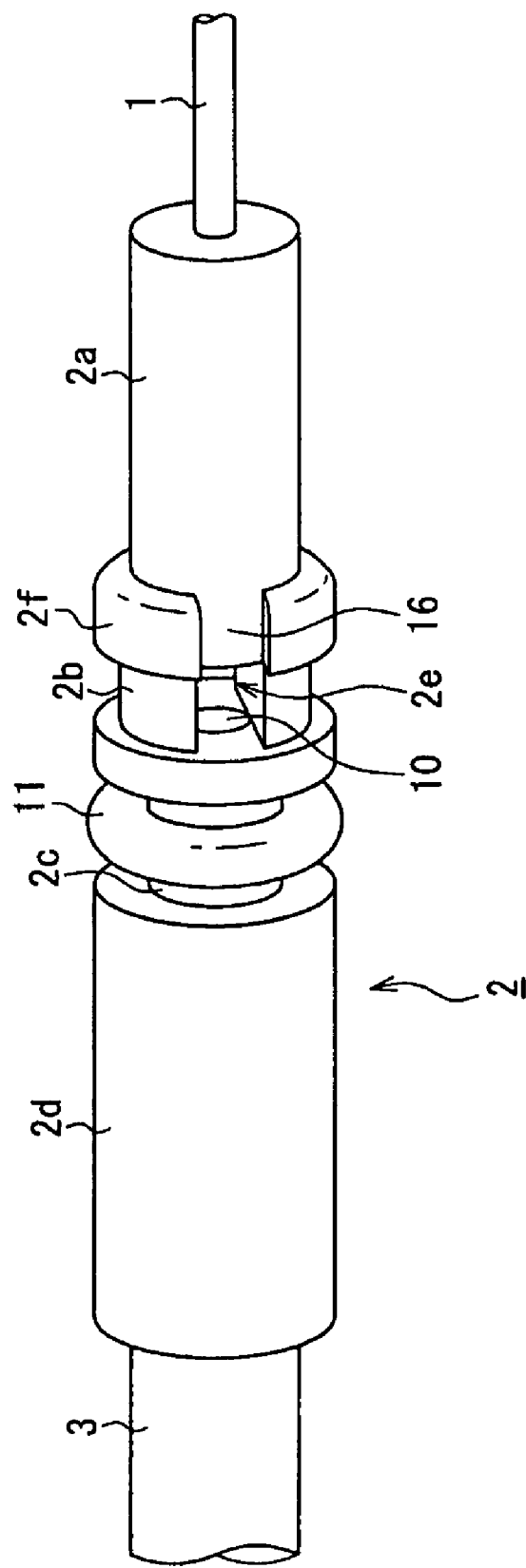
FIG. 3 is an enlarged perspective view showing a structure of an inner hub of the indwelling needle device.

An enlarged perspective view of the structure of the inner hub 2 is shown in FIG. 3. It is clear from this drawing that a space between the outer peripheral surface of the front part 2a and the inner peripheral surface of the shield tube 4a communicates via the lateral penetration path 2e with the lumen 10 of the intermediate part of the inner hub 2. Furthermore, it is clear also from the drawing that a pair of side walls are formed on both sides of the lateral penetration path 2e, and each of outer peripheral surfaces of the side walls is recessed so that the pair of engagement recesses 2b are formed. At a front-end-side position on the engagement recess 2b, a large-diameter part 2f is formed, which has the diameter of the intermediate part of the inner hub 2. In the large-diameter part 2f, axis-direction grooves 16 are formed, which extend from the front part 2a to the engagement recess 2b.

In the initial state shown in FIG. 1, the inner needle 1 is projected out of the outer needle 8 so as to be ready to puncture. In this state, the engagement recesses 2b and the front-end-side engagement projection 12a are engaged with each other, and the inner hub 2 is held at this position with respect to the shield tube 4a. Besides, since the front part 2a of the inner hub 2 has a small diameter, the front part 2a is fitted in the lumen of the rear part of the outer hub 7. This configuration makes it possible to minimize the space formed between the outer surface of the inner hub 2 and the inner surface of the shield tube 4a in this initial state. After puncturing in this state, for indwelling, the inner needle 1 is retracted so as not to be projected out of the outer needle 8, as shown in FIG. 2.

In the state shown in FIG. 2, since the front part 2a of the inner hub 2 is out of the outer hub 7, a space 14 is formed between the outer peripheral surface of the front part 2a having a small diameter and the inner peripheral surface of the shield tube 4a. This space 14 communicates with the lumen of the outer needle 8 via a space 15 formed between the outer peripheral surface of the inner needle 1 and the inner peripheral surface of the shield tube 4a. Further, the space 14 also communicates with the lumen 10 in the intermediate part of the inner hub 2 via the axis-direction groove 16 and the lateral penetration path 2e. This configuration allows the space 14 formed between the inner hub 2 and the shield tube 4a to function as a flow path in addition to the flow path formed by the lumen of the inner needle 1, thereby surely providing a greater flow rate. Still further, since the lumen 10 of the inner hub 2 is broader than the lumen of the inner needle 1, it is possible to surely provide a greater total flow rate as compared with the case where only the flow path formed by the lumen of the inner needle 1 is available.

In the state shown in FIG. 2, the engagement recess 2b and the rear-end-side engagement projection 12b are engaged with each other, whereby the inner hub 2 is held with respect to the shield tube 4a. Since the inner needle 1 is housed substantially entirely in the shield tube 4a, the possibility of accidental punctures is reduced sufficiently. The engagement recess 2b and the rear-end-side engagement projection 12b, which are engaged with each other, function in preventing the inner needle 1 from being re-projected. In this state, the rear end of the inner hub 2 is brought into contact with the stopper 13, whereby an effect of preventing the inner hub 2 from getting out of the shield tube 4a can be achieved sufficiently.

As described above, with the configuration in which the engagement recesses 2b and the lateral penetration path 2e are provided at the same position in the axis direction and the engagement recesses 2b are provided in pair, a structure can be achieved in which a sufficient flow path cross-sectional area is provided by the lateral penetration path 2e, while the connecting part between the side walls forming the engagement recesses 2b and the front part 2a has a sufficiently firm and stable structure. The reason for this is as follows: even if the lateral penetration path 2e is formed large enough, since the side walls where the engagement recesses 2b are formed are in pair, the strength is symmetric, and the stability in use can be ensured. Furthermore, since the engagement recesses 2b and the lateral penetration path 2e are provided at the same position in the axis direction, the inner hub 2 can be configured to be very small in size.

Normally, the indwelling needle device is used in a state as shown in FIG. 1. In this initial state, the engagement recesses 2b and the front-end-side engagement projection 12a are engaged with each other, whereby the inner hub 2 is held with respect to the shield tube 4a. This holding power is such that the initial state is maintained and the inner needle 1 is not retracted easily. The puncturing operation is carried out by holding the wing parts 5 and 6 upward along the outer surface of the shield tube 4a so that they are joined, and gripping the same in this state. By gripping the wing parts 5 and 6, the gripping power is transmitted to the shield tube 4a, thereby pressing and deforming the shield tube 4a. This causes a frictional contact between the inner peripheral surface of the shield tube 4a and the inner hub 2, with which the inner needle 1 is held with a sufficient power. Further, since this increases the holding power due to the engagement recesses 2b and the front-end-side engagement projection 12a, the inner needle 1 is held with a sufficient power, whereby the puncturing operation can be carried out successfully.

For indwelling after puncturing, a force for retracting the inner hub 2 into the inside of the shield tube 4a is applied via the tube 3, so that the state shown in FIG. 2 is obtained. In other words, the engagement recesses 2b and the front-end-side engagement projection 12a are disengaged, while the engagement recesses 2b and the rear-end-side engagement projection 12b are engaged with each other. This causes the inner needle 1 to be pulled out of a blood vessel, with only the outer needle 8 being indwelled in the inserted state.

When the indwelling needle device is disposed after puncturing, an accidental puncture can be prevented if it is in the state shown in FIG. 2. This is because a state in which the re-projection of the inner needle 1 is prevented is achieved since the inner needle 1 is housed in the shield tube 4a and the engagement recesses 2b and the rear-end-side engagement projection 12b are engaged with each other.

Embodiment 2

An indwelling needle device according to Embodiment 2 is described with reference to FIGS. 4 to 6. It should be noted that the same elements as those in Embodiment 1 are designated with the same reference numerals, and duplicate descriptions of the elements are omitted.

Figure 4:
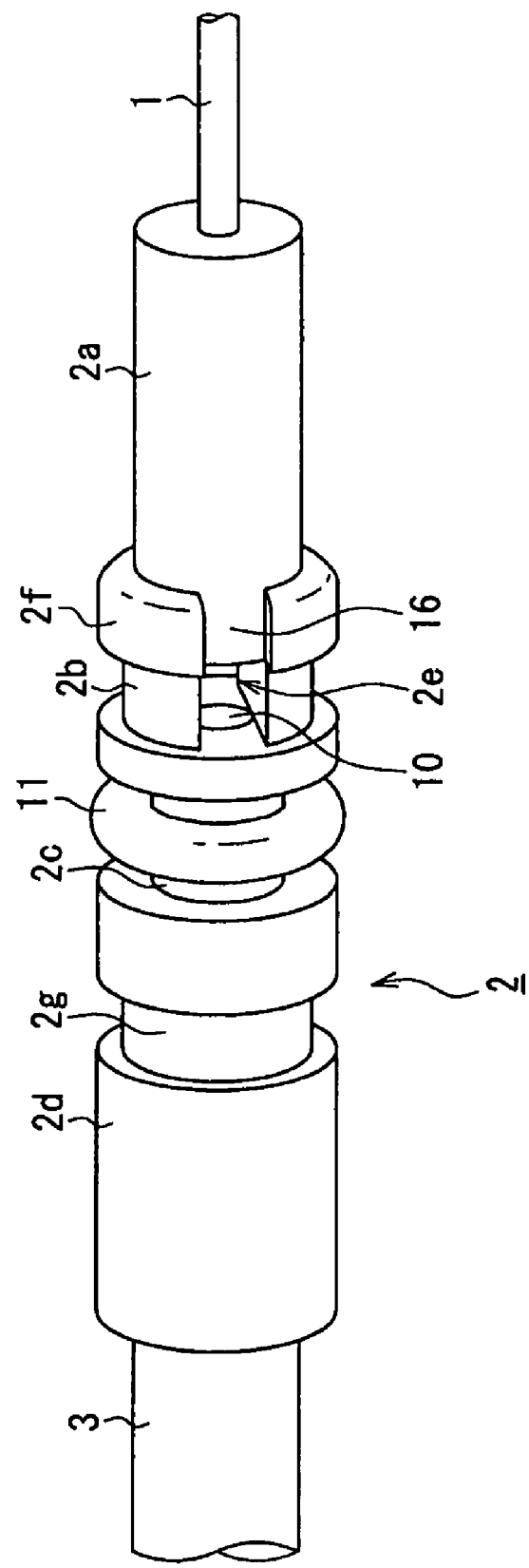
FIG. 4 is an enlarged perspective view showing a structure of an inner hub of an indwelling needle device according to Embodiment 2 of the present invention.

In the present embodiment, as shown in FIG. 4, a rear-end-side engagement recess 2g is provided on the rear part 2d of the inner hub 2, i.e., on the outer peripheral surface of the inner hub 2, at a position on the rear end side with respect to the sealing circular recess 2c. In the following description, for clear distinction, the engagement recesses 2b are referred to as front-end-side engagement recesses 2b. The rear-end-side engagement recess 2g is formed in a groove shape in the circumference direction on the outer peripheral surface of the inner hub 2.

Figure 5:
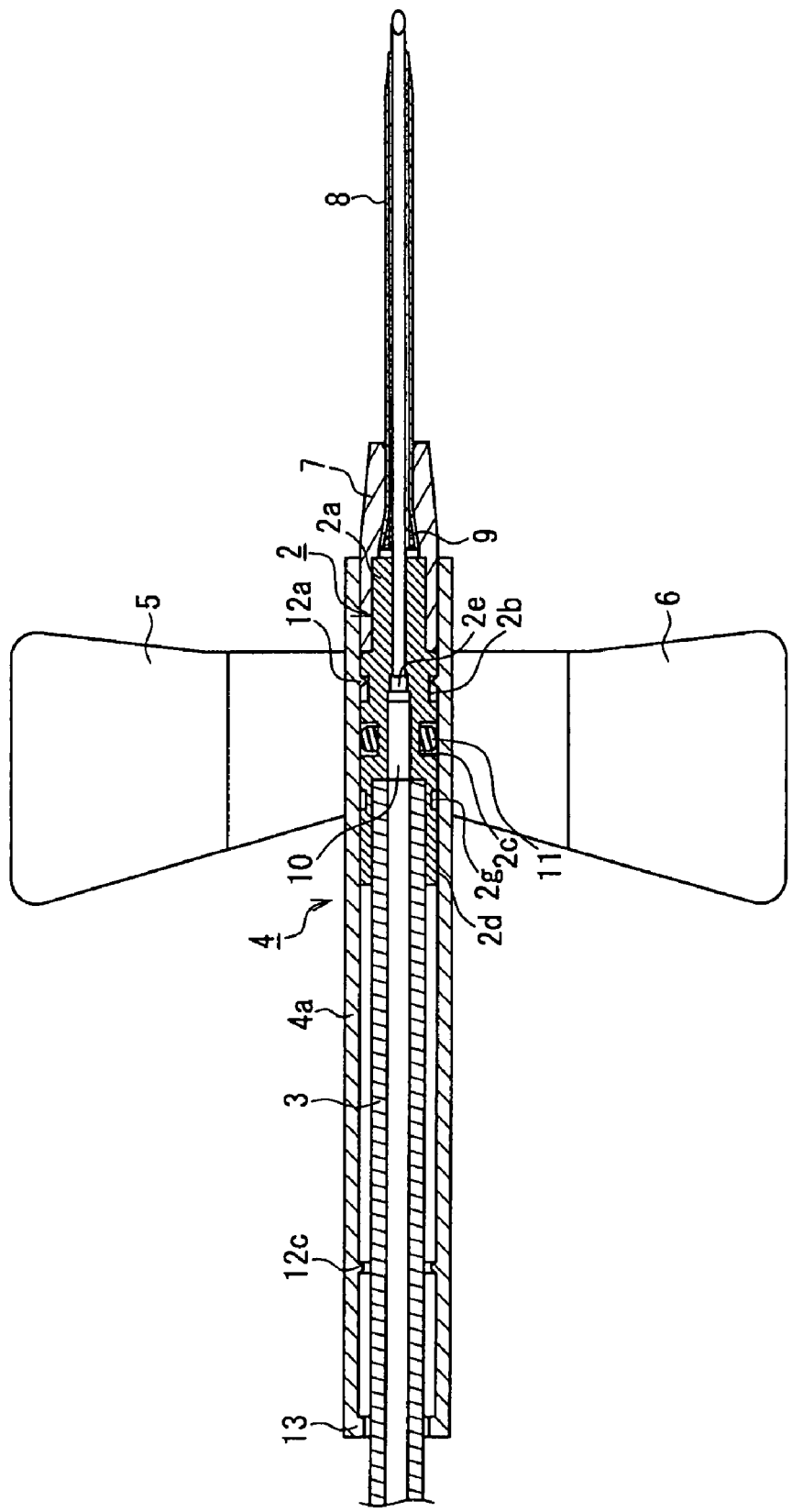
FIG. 5 is a cross-sectional view showing the indwelling needle device.

As shown in FIG. 5, the rear-end-side engagement projection 12c provided at a rear-end-side position on the inner peripheral surface of the shield tube 4a corresponds to the rear-end-side engagement recess 2g, and therefore it is formed at a position shifted toward the rear end side as compared with the rear-end-side engagement projection 12b in Embodiment 1.

The state of the indwelling needle device according to FIG. 5 is identical to the state of use (initial state) shown in FIG. 1 in the case of Embodiment 1. More specifically, the inner needle 1 is projected out of the outer needle 8 so as to be puncturable, and the front-end-side engagement recesses 2b and the front-end-side engagement projection 12a are engaged with each other, whereby at this position the inner hub 2 is held with respect to the shield tube 4a.

Figure 6:
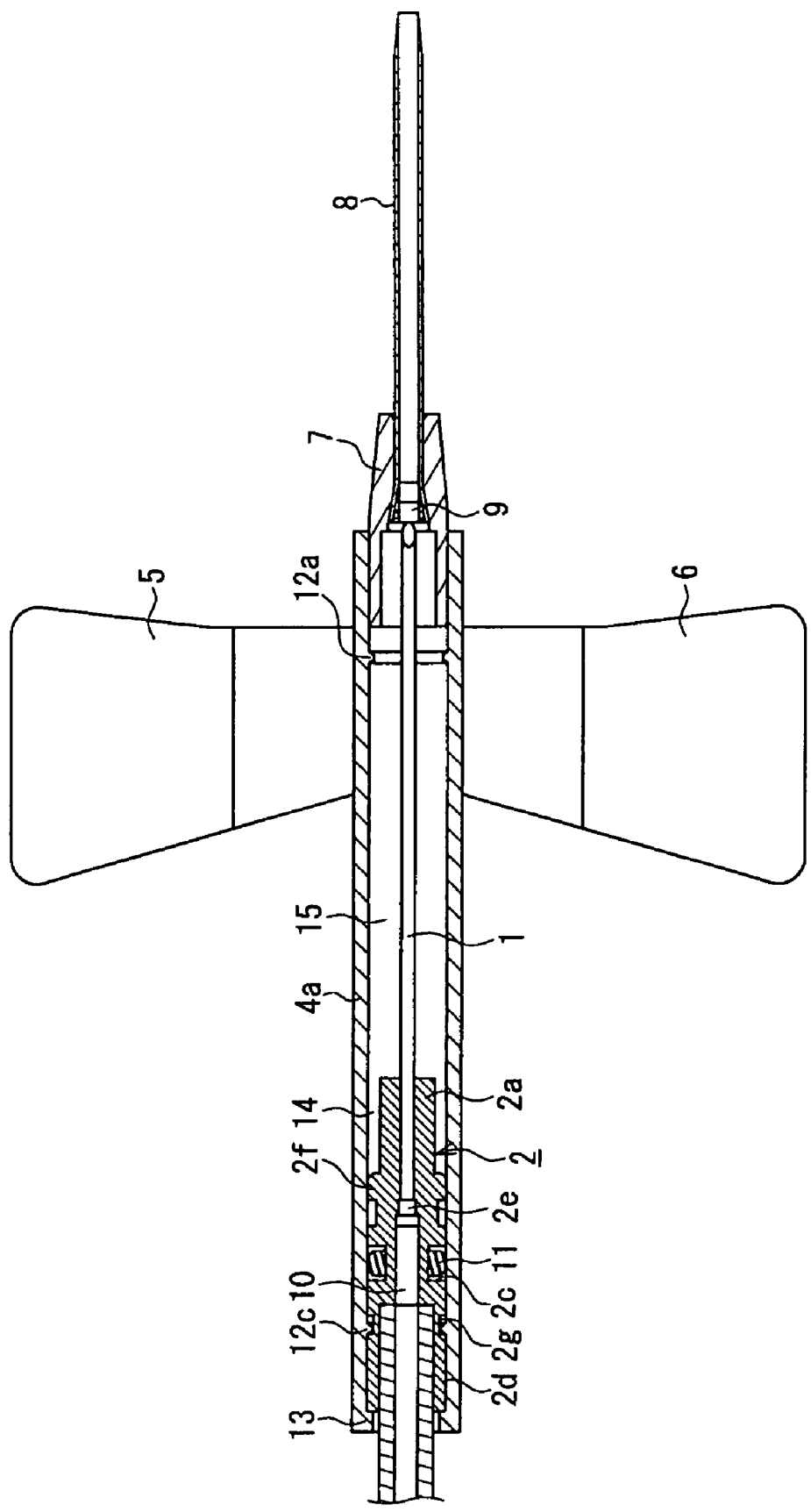
FIG. 6 is a cross-sectional view showing a state of the indwelling needle device when it is indwelled or when it is disposed.

The state shown in FIG. 6 corresponds to the state shown in FIG. 2 in Embodiment 1, in which the inner needle 1 is housed in the shield tube 4a. However, unlike Embodiment 1, the rear-end-side engagement recess 2g and the rear-end-side engagement projection 12c are engaged with each other, whereby the inner hub 2 is held with respect to the shield tube 4a. The reason why the rear-end-side engagement recess 2g is provided for the above-described holding in this state is as described below.

In Embodiment 1, the position of the engagement recesses 2b is on the front end side (on the inner needle 1 side) with respect to the sealing circular recess 2c. In the case of this embodiment, in an operation of retracting the inner hub 2 so as to house the inner needle 1, the O-ring 11 is physically brought into contact with the rear-end-side engagement projection 12b provided on an inner surface of the shield tube 4a. This could possibly twist or curl the O-ring 11, and this possibly could make it difficult to keep the air-tightness of the space 15. Still further, a feeling of the physical contact during the housing operation could possibly induce a wrong operation.

In contrast, as in the present embodiment, with a structure in which the front-end-side engagement recesses 2b and the front-end-side engagement projection 12a are engaged with each other when the inner hub 2 is placed at a front-end-side position inside the shield tube 4a (when the inner needle 1 is projected out), and the rear-end-side engagement recess 2g and the rear-end-side engagement projection 12c are engaged with each other when the inner hub 2 is placed at a rear-end-side position inside the shield tube 4a (when the inner needle 1 is housed), the above-described contact between the O-ring 11 and the rear-end-side engagement projection 12c is avoided.

Embodiment 3

An indwelling needle device according to Embodiment 3 is described with reference to FIGS. 7A to 7C. The present embodiment relates to an improvement of the inner needle 1.

Figure 7A:
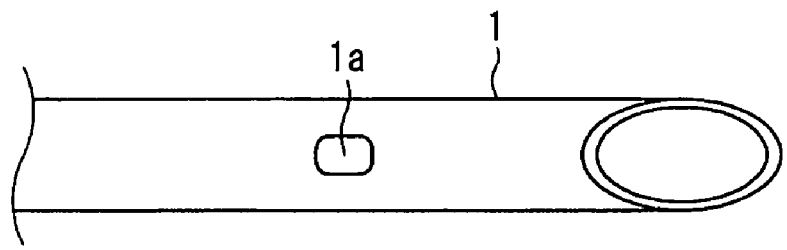
FIG. 7A is a front view showing a structure of the inner needle of the indwelling needle device according to Embodiment 3 of the present invention.
Figure 7B:
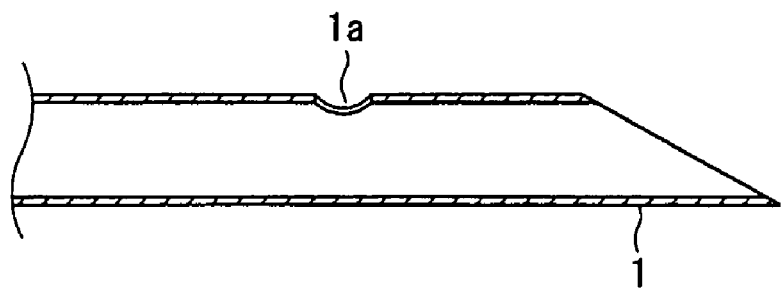
FIG. 7B is a cross-sectional view of the inner needle.
Figure 7C:
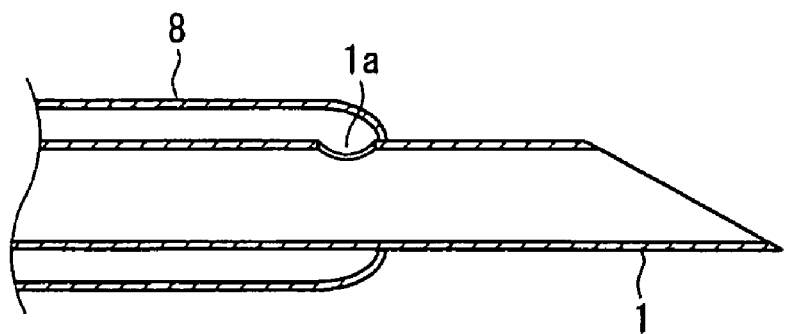
FIG. 7C is a cross-sectional view showing an effect of the inner needle.

As shown in FIGS. 7A and 7B, the inner needle 1 has a side hole 1a in its front end part. The position of the side hole 1a is determined as shown in FIG. 7C, with the relationship thereof with the outer needle 8 being taken into consideration. More specifically, the side hole 1a is formed at a position on the rear end side with respect to a position at which the front end part of the outer needle 8 is in contact with the inner needle 1 in a state in which a projected portion of the inner needle 1 out of the front end of the outer needle 8 has the maximum length. The reason why the side hole 1a is provided in this way is as follows.

When a "priming operation" for filling the indwelling needle device with physiological saline or the like is carried out, the operation is carried out in the initial state in which the inner hub 2 is positioned on the front end side in the shield tube 4a. However, if the side hole 1a is not provided, the space formed between the inner surface of the outer needle 8 and the outer surface of the inner needle 1, and the space formed between the inner surface of the shield tube 4a and the outer surface of the inner hub 2 in an area on the front end side with respect to the lateral penetration path 2e are difficult to prime, and air easily remains therein. This is because it is very difficult for air to pass through between the inner surface of the front end of the outer needle 8 and the outer surface of the inner needle 1, which are in close contact with each other. As a result, air remains in the device when the inner needle 1 is housed, and there is a possibility that this air enters the blood vessel of a patient.

In contrast, with the configuration of the present embodiment, a liquid for priming easily can flow into the space formed between the inner surface of the outer needle 8 and the outer surface of the inner needle 1 and the space formed between the inner surface of the shield tube 4a and the outer surface of the inner hub 2 in an area on the front end side with respect to the lateral penetration path 2a. Therefore, it is possible to prevent air from remaining in the indwelling needle device. To achieve this effect more sufficiently, a plurality of the side holes 1a may be provided. In this case, however, it is necessary to take the strength into consideration.

It should be noted that the same effect can be achieved with an embodiment in which the side hole 1a is provided at the same position as the position at which the inner needle 1 and the front end part of the outer needle 8 are brought into contact with each other. However, this embodiment is inappropriate in some cases since the front end part of the outer needle 8 could possibly be curled by an edge of the side hole 1a when the inner needle 1 is housed.

INDUSTRIAL APPLICABILITY

The indwelling needle device of the present invention has a double structure composed of an inner needle and an outer needle, which is configured so that a sufficient flow-path cross-sectional area is provided for flow from the outer needle to an infusion tube, nevertheless side walls of a hub where the foregoing opening is positioned are coupled stably and firmly with a front end part of the hub for holding an inner needle, and the hub can be configured to be small in size. Therefore, it is suitable for use in procedures such as infusion, blood transfusion, extracorporeal blood circulation and the like.

The invention claimed is:

1. An indwelling needle device comprising:
a shield tube in a substantially cylindrical form;
a flexible outer needle fixed at a front end part of the shield tube;
a hub inserted in a lumen of the shield tube so as to be movable in an axis direction, an infusion tube being attached to a rear end of the hub; and
a rigid inner needle that is fixed at a front end part of the hub and that is insertable into a lumen of the outer needle,
whereby when the hub is positioned in a front end part of the lumen of the shield tube, the inner needle penetrates the lumen of the outer needle and is projected out, and the inner needle can be housed in the lumen of the shield tube by moving the hub toward a rear end side of the lumen of the shield tube,
wherein
the hub is provided with a lateral penetration path that penetrates from a periphery to a lumen of the hub, so that a space formed between an outer peripheral surface of the hub and an inner peripheral surface of the shield tube communicates with the lumen of the hub via the lateral penetration path,
a sealing section is provided on the outer peripheral surface of the hub, at a position on a rear end side with respect to the lateral penetration path in the hub, so as to keep liquid tightness of the space formed between the outer peripheral surface of the hub and the inner peripheral surface of the shield tube,
an engagement recess is formed on the outer peripheral surface of the hub at the same position with respect to the axis direction as the position of the lateral penetration path in the hub, and
a rear-end-side engagement projection is formed at a rear-end-side position on the inner peripheral surface of the shield tube, so as to be engageable with the engagement recess in a state in which the inner needle is housed in the lumen of the shield tube, whereby the hub is held with respect to the shield tube, preventing the inner needle from being re-projected.

2. The indwelling needle device according to claim 1, wherein
the shield tube further includes a front-end-side engagement projection at a front-end-side position on the inner peripheral surface of the shield tube, the front-end-side engagement projection being engageable with the engagement recesses of the hub in a state in which the inner needle is projected out of the outer needle.

3. The indwelling needle device according to claim 1, wherein
the inner needle has a side hole in its front end part, the side hole being positioned on the rear end side with respect to a position at which a front end part of the outer needle is in contact with the inner needle in a state in which a projected portion of the inner needle out of an end of the outer needle has the maximum length.

4. The indwelling needle device according to claim 1, wherein
an outer diameter of the hub at a position on a front end side with respect to the lateral penetration path is smaller than an outer diameter of the hub at a position on a rear end side.

5. An indwelling needle device comprising:
a shield tube in a substantially cylindrical form;
a flexible outer needle fixed at a front end part of the shield tube;
a hub inserted in a lumen of the shield tube so as to be movable in an axis direction, an infusion tube being attached to a rear end of the hub; and
a rigid inner needle that is fixed at a front end part of the hub and that is insertable into a lumen of the outer needle,
whereby when the hub is positioned in a front end part of the lumen of the shield tube, the inner needle penetrates the lumen of the outer needle and is projected out, and the inner needle can be housed in the lumen of the shield tube by moving the hub toward a rear end side of the lumen of the shield tube,
wherein
the hub is provided with a lateral penetration path that penetrates from a periphery to a lumen of the hub, so that a space formed between an outer peripheral surface of the hub and an inner peripheral surface of the shield tube communicates with the lumen of the hub via the lateral penetration path,
a sealing section is provided on the outer peripheral surface of the hub, at a position on a rear end side with respect to the lateral penetration path in the hub, so as to keep liquid tightness of the space formed between the outer peripheral surface of the hub and the inner peripheral surface of the shield tube, a rear-end-side engagement recess is formed on the outer peripheral surface of the hub, at a position on a rear end side with respect to the sealing section, and a rear-end-side engagement projection is formed at a rear-end-side position on the inner peripheral surface of the shield tube so as to be engageable with the rear-end-side engagement recess in a state in which the inner needle is housed in the lumen of the shield tube, whereby the hub is held with respect to the shield tube, preventing the inner needle from being re-projected.

6. The indwelling needle device according to claim 2, wherein the front-end-side engagement projection and the rear-end-side engagement projection are formed as circular projections extending in a circumferential direction of the inner peripheral surface of the shield tube.

7. The indwelling needle device according to claim 1, wherein the sealing section is composed of a circular groove formed on the outer peripheral surface of the hub and an O-ring placed in the circular groove.

8. The indwelling needle device according to claim 1, wherein a diameter of the lumen of the hub at a position on the rear end side with respect to a position at which the lumen communicates with the lateral penetration path is greater than a diameter of the lumen of the inner needle, and equal to or smaller than an inner diameter of the infusion tube.

9. The indwelling needle device according to claim 1, wherein the hub further includes, on the outer peripheral surface thereof, an axis-direction groove for allowing a space formed between an outer peripheral surface of a front end part of the hub and the inner peripheral surface of the shield tube communicates with the lateral penetration path.

10. The indwelling needle device according to claims 5, wherein an outer diameter of the hub at a position on a front end side with respect to the lateral penetration path is smaller than an outer diameter of the hub at a position on a rear end side.

11. The indwelling needle device according to claim 5, wherein the front-end-side engagement projection and the rear-end-side engagement projection are formed as circular projections extending in a circumferential direction of the inner peripheral surface of the shield tube.

12. The indwelling needle device according to claim 5, wherein the sealing section is composed of a circular groove formed on the outer peripheral surface of the hub and an O-ring placed in the circular groove.

13. The indwelling needle device according to claim 5, wherein a diameter of the lumen of the hub at a position on the rear end side with respect to a position at which the lumen communicates with the lateral penetration path is greater than a diameter of the lumen of the inner needle, and equal to or smaller than an inner diameter of the infusion tube.

14. The indwelling needle device according to claim 5, wherein the hub further includes, on the outer peripheral surface thereof, an axis-direction groove for allowing a space formed between an outer peripheral surface of a front end part of the hub and the inner peripheral surface of the shield tube communicates with the lateral penetration path.

15. The indwelling needle device according to claim 5, wherein the inner needle has a side hole in its front end part, the side hole being positioned on the rear end side with respect to a position at which a front end part of the outer needle is in contact with the inner needle in a state in which a projected portion of the inner needle out of an end of the outer needle has the maximum length.

16. The indwelling needle device according to claim 5, wherein the shield tube further includes an engagement recess formed on the outer peripheral surface of the hub at the same position with respect to the axis direction as the position of the lateral penetration path in the hub; and a front-end-side engagement projection formed at a front-end-side position on the inner peripheral surface of the shield tube, the front-end-side engagement projection being engageable with the engagement recesses of the hub in a state in which the inner needle is projected out of the outer needle.

* * * * *